(12) United States Patent
Braun, Jr. et al.

(10) Patent No.: US 7,833,996 B2
(45) Date of Patent: *Nov. 16, 2010

(54) COMPOSITION AND METHOD FOR CONTROLLING RICE WATER WEEVILS

(75) Inventors: John C. Braun, Jr., Benton, AR (US); Henry R. Mitchell, Louisville, MS (US); Robert M. Herrick, Hamilton, NJ (US); D. Craig Heim, Westmont, NJ (US); Henry Stefanski, Crowley, LA (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/158,477

(22) PCT Filed: Dec. 21, 2006

(86) PCT No.: PCT/US2006/049064

§ 371 (c)(1), (2), (4) Date: Oct. 22, 2008

(87) PCT Pub. No.: WO2007/089346

PCT Pub. Date: Aug. 9, 2007

(65) Prior Publication Data

US 2009/0124500 A1    May 14, 2009

Related U.S. Application Data

(60) Provisional application No. 60/753,057, filed on Dec. 22, 2005.

(51) Int. Cl.
*A61K 31/00* (2006.01)
*A01N 31/16* (2006.01)

(52) U.S. Cl. .................. 514/183; 504/101; 514/427
(58) Field of Classification Search ............ 504/101; 514/183, 427

See application file for complete search history.

(56) References Cited

U.S. PATENT DOCUMENTS 5,189,060 A    2/1993   Kanne
6,201,008 B1 *  3/2001   Takada et al. ............... 514/427

OTHER PUBLICATIONS

Coatney, K., Western Farm Press, Feb. 17, 2001, pp. 1-2.*

* cited by examiner

*Primary Examiner*—Shaojia Anna Jiang
*Assistant Examiner*—Ganapathy Krishnan

(57) ABSTRACT

The present invention relates to an insecticidal composition comprising i) zeta cypermethrin and ii) a granular fertilizer, and a method for controlling rice water weevil comprising applying an effective amount of the composition to a rice field prior to flooding.

6 Claims, No Drawings

COMPOSITION AND METHOD FOR CONTROLLING RICE WATER WEEVILS

This application claims the benefit of U.S. Provisional Application No. 60/753,057, filed Dec. 22, 2005.

FIELD OF THE INVENTION

The present invention relates generally to compositions and methods of controlling insects. In particular, it pertains to a composition and a method useful for control of rice water weevils.

BACKGROUND OF THE INVENTION

The rice water weevil, *Lissorhoptrus oryzophilus*, is an important insect pest of rice. The rice water weevil is responsible for annual rice yield losses of 10-30% and in excess of 60% in some geographies if left untreated. For many years, the primary method for rice water weevil control was applications of granular carbofuran. However, the EPA cancelled carbofuran registration for this use in the late 1990's. Since the loss of carbofuran, liquid pyrethroid insecticides have become the main control method for rice water weevil.

Traditionally, pyrethroid insecticides are applied in a liquid spray solution by aerial application to control rice water weevil. However, under adverse conditions, this application method has the potential for off-target movement resulting in a loss of the product and potential non-target effects. An improved composition and method for application of the liquid pyrethroid insecticides is needed to avoid these potentially costly effects.

SUMMARY OF THE INVENTION

In accordance with the present invention, it has now been found that a novel composition and method useful for controlling rice water weevil minimizes off-target movement during application of insecticides as well as improving efficiency of insecticide and nutrient application. Specifically, the present invention is an insecticidal composition comprising i) a pyrethroid selected from the group consisting of bifenthrin, cypermethrin, zeta cypermethrin, lambdacyhalothrin, betacyhalothrin, alphacypermethrin, tralomethrin, deltamethrin, cyfluthrin, beta-cyfluthrin, esfenvalerate, fluvalinate, etofenprox, permethrin, metofluthrin, resmethrin, bioresmethrin, allethrin, bioallethrin, s-bioallethrin and tetramethrin and ii) a granular fertilizer, and a method for controlling rice water weevil comprising applying an effective amount of the composition to a locus where rice water weevil control is needed or expected to be needed. Other aspects of the present invention will also be apparent.

DETAILED DESCRIPTION OF THE INVENTION

It has now been unexpectedly found that an insecticidal composition comprising i) a pyrethroid selected from the group consisting of bifenthrin, cypermethrin, zeta cypermethrin, lambdacyhalothrin, betacyhalothrin, alphacypermethrin, tralomethrin, deltamethrin, cyfluthrin, beta-cyfluthrin, esfenvalerate, fluvalinate, etofenprox, permethrin, metofluthrin, resmethrin, bioresmethrin, allethrin, bioallethrin, s-bioallethrin and tetramethrin and ii) a granular fertilizer, and the use of such a composition in a method for controlling rice water weevil comprising applying an effective amount of the composition to a locus where rice water weevil control is needed or expected to be needed, result in effective control of problematic off-target movement as well as improved efficiency of the insecticide and nutrient application.

The amount of each component in the composition can vary over a wide range depending upon the required rate of pyrethroid necessary to achieve a desired level of control and the level of nutrient delivery desired. The granular fertilizer can be contacted with the pyrethroid prior to applying the composition to the locus. The locus can be any location where control of rice water weevil is desired including a rice field prior to flooding or a rice field post flood based on rice water weevil infestation levels at the time of application.

A preferred pyrethroid is bifenthrin, cypermethrin, zeta cypermethrin, lambdacyhalothrin, betacyhalothrin, alphacypermethrin, tralomethrin, deltamethrin, cyfluthrin, beta-cyfluthrin or permethrin. A more preferred pyrethroid is bifenthrin, cypermethrin, zeta cypermethrin, alphacypermethrin or permethrin. An even more preferred pyrethroid is zeta cypermethrin.

The pyrethroid can be present in a concentration of from 0.01% by weight to 1.0% by weight based upon the total weight of all components in the composition. Preferably, the pyrethroid is present in a concentration of from 0.05% by weight to 0.5% by weight based upon the total weight of all components in the composition.

The granular fertilizer can be selected from a group consisting of nitrogen, phosphate and potassium fertilizers. The granular fertilizer can be present in a concentration of from 95.0% by weight to 99.99% by weight based upon the total weight of all components in the composition.

The compositions of the present invention may be derived from commercially available formulations of insecticides. For example, bifenthrin, sold by FMC Corporation under the names and trademarks of Capture 2 EC, Brigade 2 EC, TALSTAR® GC FLOWABLE INSECTICIDE/MITICIDE, or TALSTAR ONE® MULTI-INSECTICIDE, to name a few, and zeta cypermethrin, sold by FMC Corporation under the name and trademarks of MUSTANG EW and MUSTANG MAX find utility in the present invention. Using methods known to one skilled in the art, the above-mentioned formulations of insecticides can be dispersed in an aqueous medium to provide a composition containing an insecticidally effective amount of the insecticide.

The following examples further illustrate the present invention, but, of course, should not be construed as in any way limiting its scope.

EXAMPLE 1

Control of Rice Water Weevil

POST Flood

Test compositions made up of MUSTANG MAX and urea fertilizer were prepared that provided appropriate rates of application of zeta cypermethrin. The test compositions were made up in a rotary mixer with internal spray nozzles. The fertilizer was loaded into the mixer and then the MUSTANG MAX liquid insecticide was sprayed into the mixer through the nozzles to effectively impregnate the fertilizer with the liquid insecticide. The impregnated fertilizer was then directly loaded into a plane for treatments on experimental plots. The impregnated fertilizer was applied at a rate of approximately 80 lb N/acre.

The test was performed on rice, variety Cocodrie, in Louisiana. The rice was planted at a seeding rate of 90 pounds per acre. Standard urea fertilizer was applied after planting at a rate of 120 lb N/acre. The insecticide and impregnated fertilizer were applied one (1) day after flooding. The experimental design used randomized plots with 3 treatments and 4 replications.

Three (3) core samples were taken in each experimental plot at 15, 22 and 34 days after application (DAA) of the insecticide or insecticide/fertilizer combination. The mean number of rice water weevil larvae per core was calculated for each plot based on the three (3) core samples at each sampling date. Also, yields of rice in each experimental plot were calculated.

The results, shown as an average of four replications, were compared with results observed in the same trials with an untreated control. The results and comparison are in tables 1 and 2 below.

TABLE 1

Control of Rice Water Weevil

| Treatment | Rate of (lbs AI/ Appln. Acre) | Mean number of Rice Water Weevil Larvae per core | | |
|---|---|---|---|---|
| | | 15 days after application | 22 days after application | 34 days after application |
| MUSTANG MAX | 0.023 | 7 | 31 | 11 |
| Mustang Max + Fertilizer | 0.023 | 2 | 14 | 20 |
| Untreated | 0 | 12 | 31 | 15 |

TABLE 2

Rice Yield Effects

| Treatment | Rate of Appln. (lbs AI/Acre) | Yield of Rice (pounds/Acre) |
|---|---|---|
| MUSTANG MAX | 0.023 | 3357 |
| Mustang Max + Fertilizer | 0.023 | 3365 |
| Untreated | 0 | 1452 |

EXAMPLE 2

Control of Rice Water Weevil

PRE Flood

Test compositions made up of MUSTANG MAX and urea fertilizer were prepared that provided appropriate rates of application of zeta cypermethrin. The test compositions were made up in a rotary mixer with internal spray nozzles. The fertilizer was loaded into the mixer and then the MUSTANG MAX liquid insecticide was sprayed into the mixer through the nozzles to effectively impregnate the fertilizer with the liquid insecticide. The impregnated fertilizer was then directly loaded into a plane for treatments on experimental plots. Impregnated fertilizer was applied at approximately 87 lb N/acre.

The test was performed on rice, variety Cocodrie, in Texas. The rice was planted at a seeding rate of 90 pounds per acre in League soil. Standard urea fertilizer was applied after planting at a rate of 113 lb N/acre. The insecticide and impregnated fertilizer were applied immediately before flooding. The experimental design used randomized plots with 3 treatments and 4 replications.

Five (5) core samples were taken in each experimental plot at 21 and 31 days after application (DAA) of the insecticide or insecticide/fertilizer combination. The number of rice water weevil larvae in the five core samples were counted and recorded at each sampling date. Also, yields of rice in each experimental plot were calculated.

The results, shown as an average of four replications, were compared with results observed in the same trials with an untreated control. The results and comparison are in tables 3 and 4 below.

TABLE 3

Control of Rice Water Weevil

| Treatment | Rate of Appln. (lbs AI/Acre) | Number of Rice Water Weevil Larvae | |
|---|---|---|---|
| | | 21 days after application | 31 days after application |
| MUSTANG MAX | 0.023 | 2 | 5 |
| Mustang Max + Fertilizer | 0.025 | 2 | 2 |
| Untreated | 0 | 42 | 51 |

TABLE 4

Rice Yield Effects

| Treatment | Rate of Appln. (lbs AI/Acre) | Yield of Rice (pounds/Acre) |
|---|---|---|
| MUSTANG MAX | 0.023 | 8363 |
| Mustang Max + Fertilizer | 0.023 | 8214 |
| Untreated | 0 | 7885 |

In the context of the present invention, the term "insecticide" refers to the active chemical compound or ingredient, a pyrethroid, which kills or causes knockdown of insects. The term "liquid insecticide" refers to a formulation of an insecticide where the formulation can be dispensed in an aqueous medium prior to its use. The term "locus" refers to any locations where control of insects is needed or expected to be needed. The term "% by weight" refers to the weight of the insecticide or specified component as a percent of the total weight of the composition (e.g. including the aqueous medium, other insecticides, surfactants, wetting agents, freeze/thaw agents and combinations thereof).

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. A method for controlling rice water weevil comprising applying an effective amount of an insecticidal composition comprising
   i) zeta cypermethrin and
   ii) a granular fertilizer to a rice field prior to flooding.

2. The method according to claim 1, wherein the granular fertilizer is contacted with the pyrethroid prior to applying the composition to the locus.

3. The method according to claim 1, wherein the zeta cypermethrin is present in a concentration of from 0.01% by weight to 1.0% by weight based upon the total weight of all components in the composition.

4. The method according to claim 3, wherein the zeta cypermethrin is present in a concentration of from 0.05% by weight to 0.5% by weight based upon the total weight of all components in the composition.

5. The method according to claim 1, wherein the granular fertilizer is selected from the group consisting of nitrogen, phosphate and potassium fertilizers.

6. The method according to claim 1, wherein the granular fertilizer is present in a concentration of from 95.0% by weight to 99.99% by weight based upon the total weight of all components in the composition.

* * * * *